United States Patent
Arao et al.

(10) Patent No.: US 8,372,647 B2
(45) Date of Patent: Feb. 12, 2013

(54) METHOD OF DIAGNOSING PANCREATIC CANCER WITH THE USE OF N-BINDING TYPE SUGAR CHAINS

(75) Inventors: Tokuzo Arao, Osaka (JP); Kazuko Matsumoto, Osaka (JP); Kazuto Nishio, Osaka (JP); Hiroki Sakamoto, Osaka (JP); Masayuki Kitano, Osaka (JP); Masatoshi Kudo, Osaka (JP)

(73) Assignee: Sumitomo Bakelite Company Limited, Tokyo (JP)

( * ) Notice: Subject to any disclaimer, the term of this patent is extended or adjusted under 35 U.S.C. 154(b) by 180 days.

(21) Appl. No.: 12/991,340

(22) PCT Filed: May 8, 2009

(86) PCT No.: PCT/JP2009/002019
§ 371 (c)(1),
(2), (4) Date: Nov. 5, 2010

(87) PCT Pub. No.: WO2009/136506
PCT Pub. Date: Nov. 12, 2009

(65) Prior Publication Data
US 2011/0065141 A1    Mar. 17, 2011

(30) Foreign Application Priority Data
May 9, 2008 (JP) .................. 2008-123391

(51) Int. Cl.
*G01N 33/48* (2006.01)
*G01N 24/00* (2006.01)
*C12Q 1/34* (2006.01)
*C12Q 1/37* (2006.01)

(52) U.S. Cl. .............. 436/64; 436/173; 435/18; 435/23

(58) Field of Classification Search .................. None
See application file for complete search history.

(56) References Cited

FOREIGN PATENT DOCUMENTS

| | | |
|---|---|---|
| JP | 2000-502902 | 3/2000 |
| JP | 2001-17169 | 1/2001 |
| JP | 2004-248575 | 9/2004 |
| JP | 2005-515440 | 5/2005 |
| WO | WO 02/08760 A1 | 1/2002 |
| WO | WO03/060522 | 7/2003 |
| WO | WO 2006/114659 | 11/2006 |
| WO | WO 2007/112082 A2 | 10/2007 |
| WO | WO 2009/044213 | 4/2009 |

OTHER PUBLICATIONS

Koprowski et al., "Colorectal Carcinoma Antigens Detected by Hybridoma Antibodies," Somatic Cell Genetics, vol. 5, No. 6, pp. 957-971, 1979.

Metzgar et al., "Antigens of Human Pancreatic Adenocarcinoma Cells Defined by Murine Monoclonal Antibodies," Cancer Research, 42, pp. 601-608, Feb. 1982.

Lindholm et al., "Monoclonal Antibodies Against Gastrointestinal Tumour-Associated Antigens Isolated as Monosialogangliosides," Int. Archs Allergy Appl. Immun., 71, pp. 178-181, 1983.

Chung et al., "Preparation and Basic Study of New Monoclonal Antibody Span-1 Antibody to Pancreatic Cancer Cells," The Japanese Journal of Surgery, Nihon Gekagasskai-shi, 87, p. 236, 1986.

Barrabés et al., Glycosylation of Serum Ribonuclease 1 Indicates a Major Endothelial Origin and Reveals an Increase in Core Fucosylation in Pancreatic Cancer, Apr. 2007, vol. 17, No. 4, pp. 388-400, Glycobiology.

Okuyama et al., Fucosylated Haptoglobin is a Novel Marker for Pancreatic Cancer: A Detailed Analysis of the Oligosaccharide Structure and a Possible Mechanism for Fucosylation, Jun. 1, 2006, vol. 118, No. 11, pp. 2803-2808, International Journal of Cancer.

Zhao et al., Comparative Serem Glycoproteomics Using Lectin Selected Sialic Acid Glycoproteins with Mass Spectrometric Analysis: Application to Pancreatic Cancer Serum, Jul. 1, 2006, vol. 5, No. 7, pp. 1792-1802, Journal of Proteome Research.

European Search Report from Corresponding European Application No. 09742631.6 dated Jun. 15, 2011.

Jia Zhao et al., "N-Linked Glycosylation Profiling of Pancreatic Cancer Serum Using Capillary Liquid Phase Separation Coupled with Mass Spectrometric Analysis," Journal of Proteome Research, 2007, vol. 6, pp. 1126-1138.

Olga Gornik et al., "Changes of Serum Glycans During Sepsis and Acute Pancreatitis," Glycobiology, 2007, vol. 17, No. 12, pp. 1321-1332.

*Primary Examiner* — Rebecca Prouty
*Assistant Examiner* — Paul Martin
(74) *Attorney, Agent, or Firm* — Kenneth H. Sonnenfeld; Margaret B. Brivanlou; King & Spalding

(57) ABSTRACT

The present invention provides novel markers for diagnosing pancreatic cancer, and methods for determining if a subject has pancreatic cancer utilizing the markers, etc. The methods involve comparing mass-spectrometric peaks of certain sugar chains, obtained from patients' blood and determining if there is a significant decrease in peak intensity, compared with corresponding peaks from patients without pancreatic cancer.

4 Claims, 3 Drawing Sheets

[Fig. 1]
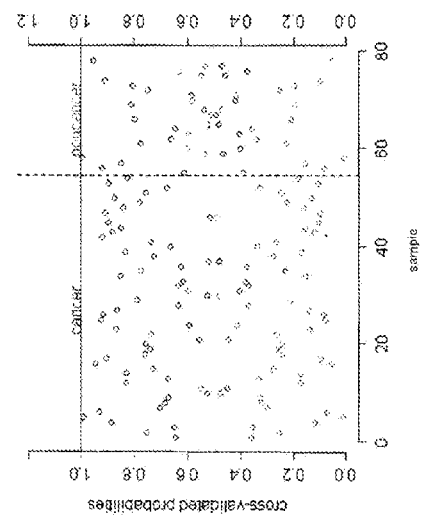
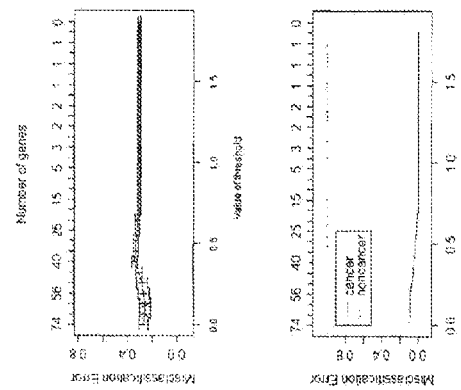
**Composition of PAM classifier:
65 genes selected by PAM (threshold equal to 0.128)**
74% correct detection rate achieved using 65 peaks

[Fig. 2]
Correct detection rate of sugar chains of m/z 3031 and m/z 2362

Composition of classifier:

Table. - Sorted by t -value:

| | t-value | p-value | % CV support | cancer | noncancer | Unique id |
|---|---|---|---|---|---|---|
| 1 | -3.01 | 0.003531 | 100 | 6.9 | 21.9 | 3031 |
| 2 | -2.44 | 0.017237 | 100 | 2.8 | 6.1 | 2362 |

Performance of the Compound Covariate Predictor Classifier.

| Class | Sensitivity | Specificity | PPV | NPV |
|---|---|---|---|---|
| cancer | 0.685 | 0.833 | 0.802 | 0.541 |
| noncancer | 0.833 | 0.685 | 0.541 | 0.902 |

Performance of the Linear Diagonal Discriminant Analysis Class

| Class | Sensitivity | Specificity | PPV | NPV |
|---|---|---|---|---|
| cancer | 0.722 | 0.792 | 0.886 | 0.559 |
| noncancer | 0.792 | 0.722 | 0.559 | 0.836 |

Performance of the 1-Nearest Neighbor Classifier.

| Class | Sensitivity | Specificity | PPV | NPV |
|---|---|---|---|---|
| cancer | 0.704 | 0.583 | 0.792 | 0.467 |
| noncancer | 0.583 | 0.704 | 0.467 | 0.792 |

Performance of the 3-Nearest Neighbors Classifier

| Class | Sensitivity | Specificity | PPV | NPV |
|---|---|---|---|---|
| cancer | 0.796 | 0.5 | 0.792 | 0.522 |
| noncancer | 0.5 | 0.796 | 0.522 | 0.792 |

Performance of the Nearest Centroid Classifier.

| Class | Sensitivity | Specificity | PPV | NPV |
|---|---|---|---|---|
| cancer | 0.648 | 0.875 | 0.921 | 0.525 |
| noncancer | 0.875 | 0.648 | 0.525 | 0.921 |

Performance of the Support Vector Machine Classifier.

| Class | Sensitivity | Specificity | PPV | NPV |
|---|---|---|---|---|
| cancer | 0.759 | 0.458 | 0.759 | 0.458 |
| noncancer | 0.458 | 0.759 | 0.458 | 0.759 |

Correct detection rate of around 70% was achieved using two peaks (m/z 3031, 2362)

[Fig. 3]

Predictive structural formulae for m/z 3031 sugar chain

| 3031 |
|---|
| (Hex)1 (HexNAc)6 (NeuGc)1 + (Man)3(GlcNAc)2 |
| (Hex)2 (HexNAc)6 (Deoxyhexose)1 + (Man)3(GlcNAc)2 |
| (HexNAc)4 (Deoxyhexose)6 + (Man)3(GlcNAc)2 |
| (HexNAc)1 (NeuAc)4 (NeuGc)1 + (Man)3(GlcNAc)2 |
| (HexNAc)1 (Deoxyhexose)2 (NeuAc)3 (NeuGc)1 + (Man)3(GlcNAc)2 |
| (Hex)1 (HexNAc)1 (Deoxyhexose)1 (NeuAc)4 + (Man)3(GlcNAc)2 |
| (Hex)1 (HexNAc)3 (NeuAc)1 (NeuGc)2 + (Man)3(GlcNAc)2 |
| (HexNAc)1 (Deoxyhexose)4 (NeuAc)2 (NeuGc)1 + (Man)3(GlcNAc)2 |
| (Hex)1 (HexNAc)1 (Deoxyhexose)3 (NeuAc)3 + (Man)3(GlcNAc)2 |
| (HexNAc)1 (Deoxyhexose)2 (NeuAc)4 + (Man)3(GlcNAc)2 |
| (Hex)1 (HexNAc)3 (NeuAc)2 (NeuGc)1 + (Man)3(GlcNAc)2 |
| (HexNAc)1 (Deoxyhexose)4 (NeuAc)3 + (Man)3(GlcNAc)2 |
| (Hex)2 (HexNAc)3 (Deoxyhexose)1 (NeuAc)2 + (Man)3(GlcNAc)2 ★ |

* shows the best possible sugar chain

[Fig. 4]

Predictive structural formulae for m/z 2362 sugar chain

| 2362 |
|---|
| (HexNAc)2 (NeuGc)2 + (Man)3(GlcNAc)2 |
| (Hex)1 (HexNAc)2 (Deoxyhexose)1 (NeuGc)1 + (Man)3(GlcNAc)2 |
| (HexNAc)2 (NeuAc)1 (NeuGc)1 + (Man)3(GlcNAc)2 |
| (Hex)1 (HexNAc)2 (Deoxyhexose)1 (NeuAc)1 + (Man)3(GlcNAc)2 ★ |

* shows the best possible sugar chain

METHOD OF DIAGNOSING PANCREATIC CANCER WITH THE USE OF N-BINDING TYPE SUGAR CHAINS

TECHNICAL FIELD

The present invention relates to a method for determining if a subject has pancreatic cancer, utilizing a specific N-linked sugar chain as a marker for diagnosing pancreatic cancer.

BACKGROUND ART

Pancreas is an organ of about 15 cm in length which is located at the back of stomach. The major pancreatic diseases are pancreatic cancer and pancreatitis. Pancreatic cancer is particularly known as one of cancers with increased mortality rate among Japanese in recent years. Causes of pancreatic cancer have not been completely identified, and excessive consumption of animal fat, animal protein, alcohol, etc. due to Westernized dietary habits, smoking and so on are considered to be risk factors. In addition, people having a history of chronic pancreatitis, pancreatolithiasis, diabetes, or acute pancreatitis are also considered to be in high-risk groups. Pancreatic cancer is initiated in cells having an exocrine function, in particular, in cells of the pancreatic duct where pancreatic juice flows, and this type accounts for more than 90% of pancreatic cancers. Early detection of pancreatic cancer is critically important, because it is highly malignant and metastasized to other organs (in particular, to the liver, etc.) at an early stage. The pancreas, however, is surrounded by many organs such as stomach, duodenum, spleen, small intestine, large intestine, liver, and gallbladder, which makes it very difficult to detect the cancer at an early stage. This often results in a distant metastasis and a pancreatic cancer discovered in an advanced stage, well past the treatable and resectable phase.

Examples of serum tumor markers that have already been developed for diagnosing pancreatic cancer include CA19-9 (Non-patent Document 1), Dupan-2 (Non-patent Document 2), CA-50 (Non-patent Document 3), Span-1 (Non-patent Document 4), etc. These markers, however, give positive results even in the cases of pancreatic and liver benign disorders such as chronic pancreatitis, chronic hepatitis, and liver cirrhosis, which poses a problem of specificity. In addition, these markers sometimes give negative results for specific pancreatic cancers, and therefore inadequate as tumor markers for specifically and reliably detecting pancreatic cancers. It has therefore been considered difficult to detect/confirm the presence of a wide range of pancreatic cancers early and reliably by conventional methods.

Further, some patent publications disclose a method for detecting and diagnosing pancreatic cancer using as a marker a gene specifically expressed on tumor cells. To date, PAN-CIA and PANCIB (Patent Document 1) and KCCR13L (Patent Document 2) have been disclosed as pancreatic cancer marker genes. Furthermore, since a DNA amplification or deletion is found in a specific chromosomal site in pancreatic cancer cells, a method is also proposed for diagnosing pancreatic cancer by detecting the amplification or deletion in the chromosomal site which is specific to pancreatic cancers (Patent Document 3).

PRIOR ART DOCUMENTS

Patent Documents

Patent Document 1: Published Japanese translation of PCT international publication 2000-502902

Patent Document 2: Japanese Patent Application No. 2003-041843
Patent Document 3: Japanese Laid-Open Patent Application No. 2001-17169

Non-Patent Documents

Non-patent Document 1: Somatic Cell Genet., 5: 957-972, 1979
Non-patent Document 2: Cancer Res., 42, 601, 1982
Non-patent Document 3: Int. Arch. Allergy Appl. Immunol., 71, 178-181, 1983
Non-patent Document 4: The Japanese Journal of Surgery (Nihon Gekagakkai-shi), 87, 236, 1986

DISCLOSURE OF THE INVENTION

Object to be Solved by the Invention

The object of the present invention is to provide a method for determining if a subject has pancreatic cancer, utilizing a novel marker for detecting pancreatic cancer.

Means to Solve the Object

The present inventors collected blood from patients of 78 cases in total including patients of 24 cases with pancreaticobiliary-duct benign disorder (16 gallstone cases and 8 pancreatitis cases) and patients of 54 cases with pancreatic cancer, and mass spectrometry was performed on N-linked sugar chains in the plasma. From 74 mass spectrometric peaks detected, 65 sugar chains were extracted based on the results of PAM analysis. These 65 sugar chains were then used for the prediction of pancreatic cancer or pancreaticobiliary-duct benign disorder, to correctly diagnose 74% cases. Further, a T-test was performed between the two groups, the group of pancreaticobiliary-duct benign disorder and the group of pancreatic cancer, which identified two sugar chains, the sugar chain of m/z 3031 and the sugar chain of m/z 2362, as sugar chains demonstrating significant difference ($p<0.05$) and exhibiting 2-fold or greater difference in expression levels between the two groups. The rate of correct detection when using these sugar chains was calculated with six classifiers, all of which showed that about 70% cases were correctly detected, and thus the present invention was completed.

More specifically, the present invention relates to (1) a method for determining if a subject has pancreatic cancer, sequentially comprising: a step of releasing N-linked sugar chains from glycoprotein in blood collected from a test subject; a step of purifying the released sugar chains; a step of performing mass spectrometry on the purified sugar chains; and a step of determining if the subject has pancreatic cancer using as an index a detected intensity of at least one sugar chain selected from sugar chains having a peak mass/charge ratio (m/z) of 3031, 2362, 1339, 3047, 2703, 2097, 1950, 1266, 3193, 4177, 2663, 2639, 2055, 2259, 2579, 1206, 2428, 1984, 2817, 1893, 2274, 2071, 2814, 2217, 2696, 1324, 2269, 2742, 2112, 2011, 2175, 2563, 2128, 2420, 2214, 4015, 2313, 1381, 2630, 1208, 1203, 3352, 2682, 3338, 2649, 2123, 2574, 2335, 2880, 1351, 2668, 2728, 4340, 2417, 1501, 1989, 2726, 1674, 1259, 3320, 1827, 1619, 1819, 2723, and 2151 in mass spectrometry using a MALDI-TOF-MS analyzer, or from sugar chains equivalent to the above sugar chains; (2) the method for determining if a subject has pancreatic cancer according to (1), wherein the peak mass/charge ratio (m/z) in mass spectrometry using the MALDI-TOF-MS analyzer is 3031 and/or 2362; and the method for determining if a subject has pancreatic cancer according to (1) or (2), wherein the N-linked sugar chains are released using trypsin and N-glycosidase F.

BRIEF DESCRIPTION OF DRAWINGS

FIG. 1 This figure shows the rate of correct detection when using 65 sugar chains extracted by PAM analysis.

FIG. 2 This figure shows the rate of correct detection by the sugar chain of m/z 3031 and the sugar chain of m/z 2362.

FIG. 3 This figure shows predictive structural formulae for the sugar chain of m/z 3031. * represents the best possible structural formula.

FIG. 4 This figure shows predictive structural formulae for the sugar chain of m/z 2362. * represents the best possible structural formula.

BEST MODE OF CARRYING OUT THE INVENTION

The method for determining if a subject has pancreatic cancer of the present invention is not particularly limited as long as it is a method sequentially comprising: (1) a step of releasing N-linked sugar chains from glycoprotein in blood collected from a test subject; (2) a step of purifying the released sugar chains; (3) a step of performing mass spectrometry on the purified sugar chains; and (4) a step of determining if the subject has pancreatic cancer using as an index a detected intensity of at least one sugar chain selected from sugar chains having a peak mass/charge ratio (m/z) of 3031, 2362, 1339, 3047, 2703, 2097, 1950, 1266, 3193, 4177, 2663, 2639, 2055, 2259, 2579, 1206, 2428, 1984, 2817, 1893, 2274, 2071, 2814, 2217, 2696, 1324, 2269, 2742, 2112, 2011, 2175, 2563, 2128, 2420, 2214, 4015, 2313, 1381, 2630, 1208, 1203, 3352, 2682, 3338, 2649, 2123, 2574, 2335, 2880, 1351, 2668, 2728, 4340, 2417, 1501, 1989, 2726, 1674, 1259, 3320, 1827, 1619, 1819, 2723, and 2151 in mass spectrometry using a MALDI-TOF-MS analyzer, or from sugar chains equivalent to the above sugar chains. A preferred method determines if a subject has pancreatic cancer using as an index a detected intensity of sugar chains with a mass spectrometric peak mass/charge ratio (m/z) of 3031 and/or 2362. Further, a sample used in the method for determining if a subject has pancreatic cancer of the present invention is not particularly limited as long as the sample is derived from the blood that have been collected from a test subject, and it may be whole blood containing all the blood components, or serum or plasma separated from the blood, while serum and plasma are preferred and plasma is particularly preferred.

In the present invention, the N-linked sugar chain is a glycoprotein sugar chain bound to an amide-group nitrogen atom on the side chain of an asparagine residue of the protein. Such sugar chain is also referred to as N-type sugar chain or asparagine-linked sugar chain. Specific examples of the method for releasing N-linked sugar chains from glycoprotein in the blood of the present invention include enzymatic methods using N-glycosidase F (also referred to as Glycopeptidase, PN Gase, glycanase, glycoamidase, etc.) or Glycopeptidase A, etc., and a hydrazinolysis methods, among which an enzymatic method using N-glycosidase F can be preferably exemplified. In association with such enzymatic method, a protease such as trypsin can be combined. Further, in the present invention, the method for purifying the released sugar chains is not particularly limited as long as it is a method wherein the sugar chains are captured and purified selectively from a mixture in a sample, while specific and preferred examples include a method using BlotGlyco (reg-istered trademark) for MALDI (Sumitomo Bakelite Co., Ltd.), that are beads for capturing sugar chains, optimized for highly-sensitive measurements by MALDI-TOF-MS.

Herein, "MALDI-TOF-MS" is an abbreviation for Matrix Assisted Laser Desorption Ionization-Time-of-Flight (Mass Spectrometer). The MALDI method comprises spotting a sample on a plate, subsequently adding a matrix solution (2,5-dihydroxybenzoic acid) thereto and then drying, hardening and crystallizing the mixture, applying a large amount of energy on the matrix by a pulsed laser irradiation so as to cause the desorption of sample-derived ions and matrix-derived ions such as $(M+H)^+$ and $(M+Na)^+$. MALDI-TOF-MS is to measure mass based on time of flight utilizing the MALDI method. When the ions are accelerated at a constant accelerating voltage V, m/z of the ions can be represented by the formula "$m/z=2eVt^2/L^2$", wherein m is mass of the ions, v is velocity of the ions, z is charge number of the ions, e is elementary electric charge, and t is time of flight of the ions.

In the present invention, other analyzer than MALDI-TOF-MS analyzer can be used. As for the ionic source, for example, electron ionization, chemical ionization, field desorption, fast atom bombardment, electrospray ionization, atmospheric pressure chemical ionization, etc. can be used. As for analysis method, for example, methods such as magnetic sector method, quadrupole method, ion trap method, and fourier transform ion cyclotron resonance method can be employed. Further, the above analysis methods can be used in combination with HPLC.

In the present invention, the sugar chain having a peak mass/charge ratio (m/z) of 3031 in mass spectrometry using a MALDI-TOF-MS analyzer is a sugar chain showing a mass spectrometric peak at m/z 3031 as a result of mass spectrometry using a MALDI-TOF-MS analyzer, and specific examples of predictive structural formulae for such sugar chain are (Hex)1(HexNAc)6(NeuGc)1+(Man)3(GlcNAc)2,
(Hex)2(HexNAc)6(Deoxyhexose)1+(Man)3(GlcNAc)2,
(HexNAc)4(Deoxyhexose)6+(Man)3(GlcNAc)2,
(HexNAc)1(NeuAc)4(NeuGc)1+(Man)3(GlcNAc)2,
(HexNAc)1(Deoxyhexose)2(NeuAc)3(NeuGc)1+(Man)3(GlcNAc)2,
(Hex)1(HexNAc)1(Deoxyhexose)1(NeuAc)4+(Man)3(GlcNAc)2,
(Hex)1(HexNAc)3(NeuAc)1(NeuGc)2+(Man)3(GlcNAc)2,
(HexNAc)1(Deoxyhexose)4(NeuAc)2(NeuGc)1+(Man)3(GlcNAc)2,
(Hex)1(HexNAc)1(Deoxyhexose)3(NeuAc)3+(Man)3(GlcNAc)2,
(HexNAc)1(Deoxyhexose)2(NeuAc)4+(Man)3(GlcNAc)2,
(Hex)1(HexNAc)3(NeuAc)2(NeuGc)1+(Man)3(GlcNAc)2,
(HexNAc)1(Deoxyhexose)4(NeuAc)3+(Man)3(GlcNAc)2,
(Hex)2(HexNAc)3(Deoxyhexose)1(NeuAc)2+(Man)3(GlcNAc)2, etc.

Further, the sugar chains equivalent to the above sugar chains mean sugar chains of the case of using other mass analyzer than MALDI-TOF-MS analyzer, that are homologous to the sugar chains showing a mass spectrometric peak at m/z 3031 when a MALDI-TOF-MS analyzer is used.

In the present invention, the sugar chain having a peak mass/charge ratio (m/z) of 2362 in mass spectrometry using a MALDI-TOF-MS analyzer is a sugar chain showing a mass spectrometric peak at m/z 2362 as a result of mass spectrometry using a MALDI-TOF-MS analyzer, and specific examples of predictive structural formulae for such sugar chain are (HexNAc)2(NeuGc)2+(Man)3(GlcNAc)2, (Hex)1(HexNAc)2(Deoxyhexose)1(NeuGc)1+(Man)3(GlcNAc)2,
(HexNAc)2(NeuAc)1(NeuGc)1+(Man)3(GlcNAc)2,
(Hex)1(HexNAc)2(Deoxyhexose)1(NeuAc)1+(Man)3(GlcNAc)2, etc.

Further, the sugar chains equivalent to the above sugar chains mean sugar chains of the case of using other mass analyzer than MALDI-TOF-MS analyzer, that are homologous to the sugar chains showing a mass spectrometric peak at m/z 2362 when a MALDI-TOF-MS analyzer is used.

The present invention will be explained more specifically by the following examples, while the technical scope of the present invention will not be limited to these exemplifications.

Example 1

Blood Collection

After obtaining informed consent from patients, blood was collected from the patients of 78 cases in total including patients of 24 cases with pancreaticobiliary-duct benign disorder (16 gallstone cases and 8 pancreatitis cases) and the patients of 54 cases with pancreatic cancer, and the plasma was centrifuged. The obtained specimens (plasma) were anonymized in a linkable fashion, and kept frozen at −80° C.

[Preparation of Blood Samples]

In order to release modified sugar chains from protein, the plasma was treated with N-glycosidase F and trypsin. Specifically, to a 100 μL of plasma, pure water (165 μL), 1M ammonium bicarbonate (25 μL), and 120 mM dithiothreitol (25 μL) were added, and the mixture was allowed to stand for 30 minutes at 60° C. Then, 123 mM iodoacetamide (50 μL) was added, and the resultant mixture was allowed to stand under shade for 1 hour at room temperature. Subsequently, trypsin (2000 units, 25 μL) was added, and the resultant mixture was allowed to stand for 1 hour at 37° C. and then heated for 15 minutes at 80° C. to denaturalize trypsin. After cooled to room temperature, the mixture was added with N-glycosidase F (10 units, 10 μL) and allowed to stand overnight at 37° C. The resultant was heated for 15 minutes at 80° C. to denaturalize the enzyme and to obtain an enzymatically-treated plasma sample of final volume of 400 μL. Further, internal standard glucose oligomer (1 to 20) (Seikagaku Corporation, #800111) was dissolved in pure water to the concentration of 10 mg/mL to prepare an internal standard sugar chain solution. To a 95 μL of the enzymatically-treated plasma sample, 5 μL (equivalent to 50 μg) of the internal standard sugar chain solution was added to prepare a solution of a final volume of 100 μL. 20 μL of the solution was treated with beads for capturing sugar chain (BlotGlyco (registered trademark) for MALDI (Sumitomo Bakelite Co., Ltd.)) to capture the released sugar chains which were then labeled.

[Analysis of Sugar-Chain Analytical Results]

The sugar chains captured by the beads were purified and separated, and subjected to mass spectrometry by a MALDI-TOF-MS analyzer (Voyager-DETM STR Workstation; Applied Biosystems) to identify 454 peaks from the obtained mass spectra, among which, 108 sugar chains were confirmed to be involved in 25% cases. From the 108 sugar chains, internal standard sugar chains, etc. were excluded, and the remaining 74 sugar chains were subjected to analysis. Each sugar chain was quantified by comparing with the internal standard and then PAM analysis (Prediction Analysis for Microarrays) was performed to extract 65 sugar chains shown in Table 1. A cross validation was performed using these 65 sugar chains, which gave the result of correct diagnosis of 58 cases (74%) out of 78 cases (FIG. 1).

TABLE 1

|  | Pancreatic cancer | Benign disorder | Measurement value for sugar chain (m/s) |
| --- | --- | --- | --- |
| 1 | 6.9 | 21.9 | 3031 |
| 2 | 2.8 | 6.1 | 2362 |
| 3 | 5.2 | 2.9 | 1339 |
| 4 | 5.3 | 10 | 3047 |
| 5 | 3.4 | 2.1 | 2703 |
| 6 | 32.3 | 46.7 | 2097 |
| 7 | 3.4 | 5.4 | 1950 |
| 8 | 2.1 | 1.3 | 1266 |
| 9 | 3.9 | 6.2 | 3193 |
| 10 | 2.2 | 3.3 | 4177 |
| 11 | 2.2 | 1.4 | 2663 |
| 12 | 2.6 | 1.7 | 2639 |
| 13 | 274.3 | 381.5 | 2055 |
| 14 | 42.3 | 56.1 | 2259 |
| 15 | 5.7 | 8.6 | 2579 |
| 16 | 4.3 | 3.1 | 1206 |
| 17 | 27.3 | 47.9 | 2428 |
| 18 | 17.2 | 11 | 1984 |
| 19 | 2 | 1.4 | 2817 |
| 20 | 248.2 | 330.2 | 1893 |
| 21 | 2.8 | 4 | 2274 |
| 22 | 22 | 30.3 | 2071 |
| 23 | 1.5 | 1.9 | 2814 |
| 24 | 113.9 | 140.5 | 2217 |
| 25 | 30.6 | 23.5 | 2696 |
| 26 | 3.5 | 2.7 | 1324 |
| 27 | 1.7 | 2.3 | 2269 |
| 28 | 6.1 | 4.7 | 2742 |
| 29 | 6.1 | 7.7 | 2112 |
| 30 | 3 | 2.4 | 2011 |
| 31 | 15.2 | 20.2 | 2175 |
| 32 | 2.6 | 3.4 | 2563 |
| 33 | 71.7 | 56.5 | 2128 |
| 34 | 17.4 | 21.7 | 2420 |
| 35 | 1.8 | 1.5 | 2214 |
| 36 | 5 | 6.1 | 4015 |
| 37 | 5.5 | 6.5 | 2313 |
| 38 | 1.7 | 1.5 | 1381 |
| 39 | 10.2 | 8.4 | 2630 |
| 40 | 6.8 | 5.4 | 1208 |
| 41 | 76 | 64.6 | 1203 |
| 42 | 21.1 | 27.3 | 3352 |
| 43 | 2072.2 | 1771.8 | 2682 |
| 44 | 3 | 2.5 | 3338 |
| 45 | 1.6 | 1.9 | 2649 |
| 46 | 3.7 | 4.4 | 2123 |
| 47 | 1.6 | 1.8 | 2574 |
| 48 | 3 | 2.6 | 2335 |
| 49 | 4.1 | 4.9 | 2880 |
| 50 | 8.1 | 7.2 | 1351 |
| 51 | 58.9 | 52.8 | 2668 |
| 52 | 84.7 | 77.2 | 2728 |
| 53 | 2.8 | 3.1 | 4340 |
| 54 | 5.1 | 4.6 | 2417 |
| 55 | 9.2 | 8.5 | 1501 |
| 56 | 2.9 | 2.7 | 1989 |
| 57 | 57.4 | 61.5 | 2726 |
| 58 | 4 | 4.4 | 1674 |
| 59 | 201.2 | 214.1 | 1259 |
| 60 | 1.8 | 1.7 | 3320 |
| 61 | 16.5 | 15.7 | 1827 |
| 62 | 1.6 | 1.7 | 1619 |
| 63 | 19.4 | 18.2 | 1819 |
| 64 | 3.5 | 3.3 | 2723 |
| 65 | 3.7 | 3.5 | 2151 |

Further, as shown in Table 2, the sensitivity and the specificity of the PAM analysis using the 65 sugar chains in the diagnosis of pancreatic cancer was 0.907 and 0.375, respectively.

TABLE 2

| Class | Sensitivity | Specificity | PPV | NPV |
|---|---|---|---|---|
| Pancreatic cancer | 0.907 | 0.375 | 0.766 | 0.643 |
| Benign disorder | 0.375 | 0.907 | 0.643 | 0.766 |

Further, a T-test was performed between the two groups, the group of pancreaticobiliary-duct benign disorder and the group of pancreatic cancer, which identified two sugar chains, the sugar chain of m/z 3031 and the sugar chain of m/z 2362, as the sugar chains exhibiting significant difference (p<0.05) and exhibiting 2-fold or greater difference in expression levels between the two groups. Table 3 shows the detected intensities of these two sugar chains, which were quantified (%) using the control as the standard (100%).

TABLE 3

| | Pancreatic cancer | Benign disorder |
|---|---|---|
| 3031 m/z | 6.9 | 21.9 |
| 2362 m/z | 2.8 | 6.1 |

Further, the rate of correct detection when using the sugar chain of m/z 3031 and the sugar chain of m/z 2362 was calculated by six classifiers, all of which gave the result of about 70% correct detection. The six classifiers used and the calculated rates of correct detection for respective classifiers are as follows:
Compound Covariate Predictor: 73%
Diagonal Linear Discriminant Analysis: 74%
1-Nearest Neighbor Predictor: 67%
3-Nearest Neighbor Predictor: 71%
Nearest Centroid Predictor: 72%
Support Vector Machine Predictor: 67%

Further, the structural formulae of the sugar chains were predicted using GlycoSuite online database (Proteome Systems), based on the signals obtained as a result of mass spectrometry (FIGS. 3 and 4). The above results revealed that using as indexes the sugar chain of m/z 3031 and the sugar chain of m/z 2362 in the plasma allows the diagnosis of pancreatic cancer.

INDUSTRIAL APPLICABILITY

According to the present invention, by analyzing a specific N-linked sugar chain in the plasma, a highly specific determination if a subject has pancreatic cancer is enabled without placing a heavy burden on a test subject.

The invention claimed is:

1. A method for determining if a subject has pancreatic cancer, sequentially comprising the following steps (1) to (4):
 (1) a step of releasing N-linked sugar chains from glycoprotein in blood collected from a test subject;
 (2) a step of purifying the released sugar chains;
 (3) a step of performing mass spectrometry on the purified sugar chains; and
 (4) a step of determining if the subject has the pancreatic cancer using as an index a significant decrease of detected intensity of sugar chains having a peak mass/charge ratio (m/z) of 3031 and 2362 in mass spectrometry using a MALDI-TOF-MS analyzer, compared to that of a patient with pancreaticobiliary-duct benign disorder;
 wherein the peak mass/charge ratio (m/z) in the mass spectrometry is a level obtained when capturing and labeling the released sugar chains using beads for capturing sugar chains.

2. The method for determining if a subject has pancreatic cancer according to claim 1, wherein the N-linked sugar chains are released using trypsin and N-glycosidase F.

3. The method according to claim 1, wherein a predictive sugar chain having a peak mass/charge ratio (m/z) of 3031 in mass spectrometry using a MALDI-TOF-MS analyzer is
 (Hex)1(HexNAc)6(NeuGc)1+(Man)3(GlcNAc)2,
 (Hex)2(HexNAc)6(Deoxyhexose)1+(Man)3(GlcNAc)2,
 (HexNAc)4(Deoxyhexose)6+(Man)3(GlcNAc)2,
 (HexNAc)1(NeuAc)4(NeuGc)1+(Man)3(GlcNAc)2,
 (HexNAc)1(Deoxyhexose)2(NeuAc)3(NeuGc)1+(Man)3(GlcNAc)2,
 (Hex)1(HexNAc)1(Deoxyhexose)1(NeuAc)4+(Man)3(GlcNAc)2,
 (Hex)1(HexNAc)3(NeuAc)1(NeuGc)2+(Man)3(GlcNAc)2,
 (HexNAc)1(Deoxyhexose)4(NeuAc)2(NeuGc)1+(Man)3(GlcNAc)2,
 (Hex)1(HexNAc)1(Deoxyhexose)3(NeuAc)3+(Man)3(GlcNAc)2,
 (HexNAc)1(Deoxyhexose)2(NeuAc)4+(Man)3(GlcNAc)2,
 (Hex)1(HexNAc)3 (NeuAc)2(NeuGc)1+(Man)3(GlcNAc)2,
 (HexNAc)1(Deoxyhexose)4(NeuAc)3+(Man)3(GlcNAc)2, or
 (Hex)2(HexNAc)3(Deoxyhexose)1(NeuAc)2+(Man)3(GlcNAc)2.

4. The method according to claim 1, wherein a predictive sugar chain having a peak mass/charge ratio (m/z) of 2362 in mass spectrometry using a MALDI-TOF-MS analyzer is
 (HexNAc)2(NeuGc)2+(Man)3 (GlcNAc)2,
 (Hex)1(HexNAc)2(Deoxyhexose)1(NeuGc)1+(Man)3(GlcNAc)2,
 (HexNAc)2(NeuAc)1(NeuGc)1+(Man)3(GlcNAc)2, or
 (Hex)1(HexNAc)2(Deoxyhexose)1(NeuAc)1+(Man)3(GlcNAc)2.

* * * * *

UNITED STATES PATENT AND TRADEMARK OFFICE
CERTIFICATE OF CORRECTION

PATENT NO. : 8,372,647 B2  
APPLICATION NO. : 12/991340  
DATED : February 12, 2013  
INVENTOR(S) : Tokuzo Arao et al.

It is certified that error appears in the above-identified patent and that said Letters Patent is hereby corrected as shown below:

In the Claims:

Column 8, claim 1, line 13, after the term "chains" please insert --for MALDI--.

Column 8, claim 3, lines 20-41, the terms

"(Hex)1(HexNAc)6(NeuGc)1+(Man)3(GlcNAc)2, (Hex)2(HexNAc)6(Deoxyhexose)1+(Man)3(GlcNAc)2, (HexNAc)4(Deoxyhexose)6+(Man)3(GlcNAc)2, (HexNAc)1(NeuAc)4(NeuGc)1+(Man)3(GlcNAc)2, (HexNAc)1(Deoxyhexose)2(NeuAc)3(NeuGc)1+(Man)3(GlcNAc)2, (Hex)1(HexNAc)1(Deoxyhexose)1(NeuAc)4+(Man)3(GlcNAc)2, (Hex)1(HexNAc)3(NeuAc)1(NeuGc)2+(Man)3(GlcNAc)2, (HexNAc)1(Deoxyhexose)4(NeuAc)2(NeuGc)1+(Man)3(GlcNAc)2, (Hex)1(HexNAc)1(Deoxyhexose)3(NeuAc)3+(Man)3(GlcNAc)2, (HexNAc)1(Deoxyhexose)2(NeuAc)4+(Man)3(GlcNAc)2, (Hex)1(HexNAc)3 (NeuAc)2(NeuGc)1+(Man)3(GlcNAc)2, (HexNAc)1(Deoxyhexose)4(NeuAc)3+(Man)3(GlcNAc)2, or (Hex)2(HexNAc)3(Deoxyhexose)1(NeuAc)2+(Man)3(GlcNAc)2."

should read

Signed and Sealed this  
Seventh Day of May, 2013

Teresa Stanek Rea  
*Acting Director of the United States Patent and Trademark Office*

--(Hex)1(HexNAc)6(NeuGc)1+(Man)3(GlcNAc)2, (Hex)2(HexNAc)6(Deoxyhexose)1+(Man)3(GlcNAc)2, (HexNAc)4(Deoxyhexose)6+(Man)3(GlcNAc)2, (HexNAc)1(NeuAc)4(NeuGc)1+(Man)3(GlcNAc)2, (HexNAc)1(Deoxyhexose)2(NeuAc)3(NeuGc)1+(Man)3(GlcNAc)2, (Hex)1(HexNAc)1(Deoxyhexose)1(NeuAc)4+(Man)3(GlcNAc)2, (Hex)1(HexNAc)3(NeuAc)1(NeuGc)2+(Man)3(GlcNAc)2, (HexNAc)1(Deoxyhexose)4(NeuAc)2(NeuGc)1+(Man)3(GlcNAc)2, (Hex)1(HexNAc)1(Deoxyhexose)3(NeuAc)3+(Man)3(GlcNAc)2, (HexNAc)1(Deoxyhexose)2(NeuAc)4+(Man)3(GlcNAc)2, (Hex)1(HexNAc)3(NeuAc)2(NeuGc)1+(Man)3(GlcNAc)2, (HexNAc)1(Deoxyhexose)4(NeuAc)3+(Man)3(GlcNAc)2, or (Hex)2(HexNAc)3(Deoxyhexose)1(NeuAc)2+(Man)3(GlcNAc)2. --

Column 8, claim 4, lines 45-50, the terms

"(HexNAc)2(NeuGc)2+(Man)3(GlcNAc)2, (Hex)1(HexNAc)2(Deoxyhexose)1(NeuGc)1+(Man)3(GlcNAc)2, (HexNAc)2(NeuAc)1(NeuGc)1+(Man)3(GlcNAc)2, or (Hex)1(HexNAc)2(Deoxyhexose)1(NeuAc)1+(Man)3(GlcNAc)2."

should read

--(HexNAc)2(NeuGc)2+(Man)3(GlcNAc)2, (Hex)1(HexNAc)2(Deoxyhexose)1(NeuGc)1+(Man)3(GlcNAc)2, (HexNAc)2(NeuAc)1(NeuGc)1+(Man)3(GlcNAc)2, or (Hex)1(HexNAc)2(Deoxyhexose)1(NeuAc)1+(Man)3(GlcNAc)2.--